(12) United States Patent
Greenberg et al.

(10) Patent No.: US 9,358,339 B2
(45) Date of Patent: Jun. 7, 2016

(54) PARTICLE BASED BIOLOGICALLY ACTIVE MOLECULE DELIVERY SYSTEMS

(71) Applicant: Bay Genomics, LLC, El Cerrito, CA (US)

(72) Inventors: Kenneth Greenberg, Berkeley, CA (US); Scott Geller, El Cerrito, CA (US)

(73) Assignee: Bay Genomics, LLC, Berkeley, CA (US)

( * ) Notice: Subject to any disclaimer, the term of this patent is extended or adjusted under 35 U.S.C. 154(b) by 42 days.

(21) Appl. No.: 14/104,804

(22) Filed: Dec. 12, 2013

(65) Prior Publication Data
US 2014/0193907 A1    Jul. 10, 2014

Related U.S. Application Data

(60) Provisional application No. 61/737,650, filed on Dec. 14, 2012, provisional application No. 61/786,150, filed on Mar. 14, 2013.

(51) Int. Cl.
*A61M 5/20*    (2006.01)
*A61M 5/30*    (2006.01)
*A61M 37/00*   (2006.01)

(52) U.S. Cl.
CPC ........... *A61M 5/2046* (2013.01); *A61M 5/3015* (2013.01); *A61M 37/00* (2013.01)

(58) Field of Classification Search
CPC .. A61M 5/2046; A61M 5/3015; A61M 37/00
See application file for complete search history.

(56) References Cited

U.S. PATENT DOCUMENTS

| | | | |
|---|---|---|---|
| 5,525,510 A | 6/1996 | McCabe et al. | |
| 5,780,100 A | 7/1998 | McCabe et al. | |
| 7,892,836 B2 | 2/2011 | Groisman et al. | |
| 2010/0305505 A1* | 12/2010 | Ducharme et al. | 604/118 |
| 2012/0135526 A1* | 5/2012 | Greenberg | 435/459 |

* cited by examiner

*Primary Examiner* — Scott Long
(74) *Attorney, Agent, or Firm* — Morrison & Foerster LLP

(57) ABSTRACT

Described here are devices and methods for the delivery of molecules, including biologically active molecules, into tissues. The devices and methods are generally particle based, and devised to deploy the molecules into a target tissue in a controlled manner to minimize tissue damage. The devices and methods may further be devised to tailor molecule delivery parameters to a variety of tissue types. Kits including various device components are also described.

18 Claims, 13 Drawing Sheets

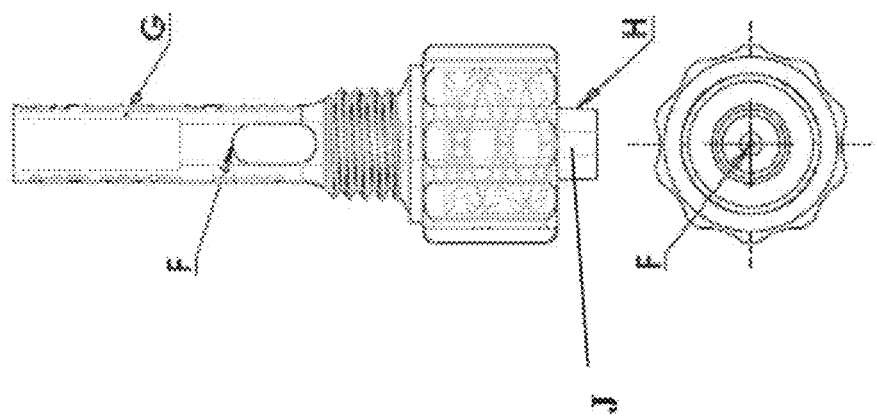
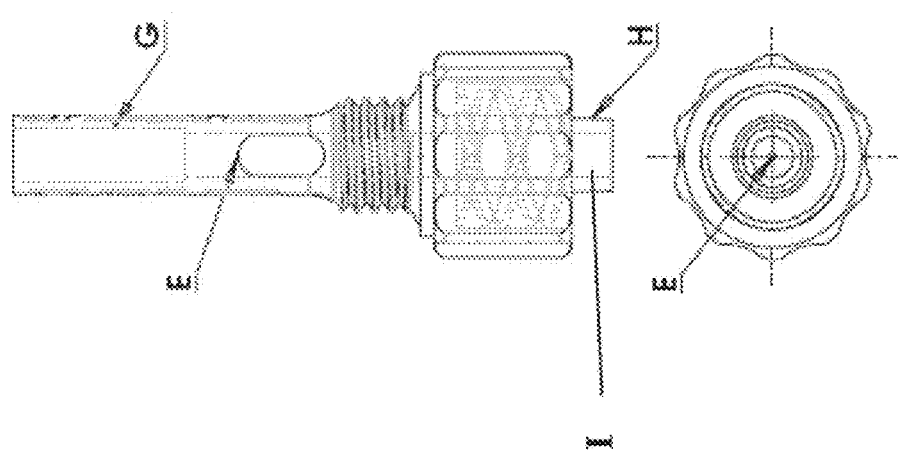

PARTICLE BASED BIOLOGICALLY ACTIVE MOLECULE DELIVERY SYSTEMS

CROSS-REFERENCE TO RELATED APPLICATIONS

This application claims priority to U.S. Provisional Application No. 61/737,650 filed on Dec. 14, 2012 and U.S. Provisional Application No. 61/786,150 filed on Mar. 14, 2013, the disclosures of which are hereby incorporated by reference in their entirety.

FIELD

Described here are devices and methods for the delivery of molecules, including biologically active molecules, into tissues. The devices and methods are generally devised to deploy the molecules into a target tissue in a controlled manner to minimize tissue damage, while maximizing delivery precision and penetration depth. The devices and methods may further be devised to tailor molecule delivery parameters to a variety of tissue types. Kits including various device components are also described.

BACKGROUND

Recent advancements in molecular biology have provided a number of techniques for manipulating the genetic material of a cell or organism. A particular subset of genetic engineering technology has facilitated the introduction of foreign genes in cells to alter their biological characteristics and morphology. The introduction of foreign genes in host cells within plants, for example, has been shown to improve vital traits such as insect resistance, frost resistance, and nutrient compositions. Another subset of genetic engineering technology seeks to read out the physiological state of a cell (e.g., biomarkers, physiological probes, reporters, indicator dyes, etc.), rather than to alter biological characteristics. Particularly useful in neuroscience and translational research, this molecular tool subset enables the visualization of various cellular changes including pH, cAMP, calcium, and membrane voltage. In recent years, the introduction of foreign genetic material in the form of gene therapy has been applied in treating diseased human tissue both in vivo and in vitro.

The introduction of foreign genetic material into a cell is commonly referred to as gene "transformation" in bacterial cells and gene "transfection" in animal cells. Both gene transformation and gene transfection can be conducted using several different approaches. One approach utilizes bacterial plasmids or viral vectors as carriers for delivering genes into cells. Other approaches, such as electroporation and microinjection, involve the physical disruption of a cell membrane to allow the introduction of foreign genetic material. Electroporation involves the use of electrical impulses to increase cell membrane and cell wall permeability to DNA contained in a solution surrounding the cell. Microinjection is a technique involving the injection of DNA directly into a cell nucleus using an ultrafine needle. Lipofection, also known as liposome transfection, is a technique used to introduce foreign genetic material into a cell by means of liposomes, which are vesicles that possess phospholipid bilayers, for example, that can fuse with a cell membrane.

Transfection by particle bombardment is a physical method of gene transfection in which high density, sub-cellular sized particles coated with foreign genetic material are accelerated to high velocity to carry the genetic material into cells. Because particle bombardment transfection does not depend on specific receptors or biochemical features typically present on cell surfaces, it can be readily applied to a variety of biological systems including plants and mammalian tissue. Also, since particle bombardment transfection involves the delivery of particles to cells at high velocity, it can overcome physical barriers to effective gene transfer, such as the stratum corneum of the epidermis, inner limiting membrane of the retina, and the cell wall of plants. In order to generate high velocity particles, known delivery systems typically subject the particles to the flow of a highly pressurized gas. However, the highly pressurized gas can cause substantial tissue damage if its pressure is not reduced before it contacts the tissue.

Accordingly, it would be useful to have delivery devices and methods that are capable of delivering molecules into tissues with minimal or no tissue damage. Particle based delivery devices and methods may be particularly useful. It would also be beneficial to have particle based delivery devices that can be operated to tailor operating parameters to particular tissues and research situations. Kits including these devices would also be useful.

SUMMARY

The devices described here may be particle bombardment based molecule delivery devices that are configured to deliver biologically active molecules (BAM) including nucleic acids, proteins, peptides, probes, dyes, dendrimers, biologics, synthetic molecules, carbohydrates, pharmaceuticals and other drugs to biological tissues in vivo, ex vivo, and in vitro. Similar to traditional particle bombardment (aka gene guns) devices, a BAM payload may be complexed onto the surface of gold or tungsten micro/nano-particles and subsequently propelled at high velocity into a target tissue via a pressurized gas source. However, unlike these known particle bombardment devices, the devices described herein incorporate multiple systems that may enable direct BAM injection to a target tissue via a needle, catheter, or cannula with minimal or no tissue damage. The integration of operating parameters of the systems, e.g., by a control module, enable the user to control BAM delivery performance and characteristics, which can be tailored to the wide variety of potential target tissues throughout the body (e.g. muscle, connective tissue, skin, nervous tissue, etc.). It is understood that in some instances the devices deliver a BAM that is not associated with a particle in the same manner as a particle based system.

The particle based delivery devices described herein may generally include a source of pressurized gas for acceleration of a particle, the particle comprising a biologically active molecule; a handpiece having an elongate body, the elongate body comprising a proximal end, a distal end, and a particle acceleration lumen therebetween in fluid communication with the pressurized gas source; a pressure relief system comprising at least one pressure relief valve for reducing gas pressure within a portion of the particle acceleration lumen; a vacuum system; a device interface configured to receive input from a user, where the input defines one or more operating parameters of the pressure relief system and the vacuum system; and a control module linked to the device interface, and configured to execute the one or more operating parameters of the systems according to the user input. The source of pressurized gas may include any suitable gas, e.g., nitrogen, argon, xenon, carbon, dioxide, air, helium, or a mixture thereof.

The devices described here generally include a delivery conduit for delivering particles to a target tissue. The delivery conduit may be a needle, cannula, or catheter. When provided as a needle, the delivery conduit may be releasably secured to the device headpiece using an adapter. The needle adapter generally has a proximal end and a distal end, and in some variations an inner barrel exists in fluid communication with the needle lumen. The inner barrel of the needle adapter may extend past the distal end of the adapter. In these instances, the inner barrel of the needle adapter may be a particle delivery lumen or a vacuum delivery lumen. In other variations, the needle adapter may comprise a single central lumen having a constant diameter. In yet further variations, the inner barrel of the needle adapter may comprise a tapered lumen.

In other variations, the delivery device for delivering molecules may include a source of pressurized gas for acceleration of a molecule; a handpiece having a body, the body comprising a proximal end, a distal end, and an acceleration lumen therebetween in fluid communication with the pressurized gas source; a device interface configured to receive input from a user, where the input defines one or more operating parameters of a plurality of device systems; and a control module linked to the device interface, and configured to execute the one or more operating parameters of the systems according to the user input to generate a pulse pattern.

With respect to operating parameters, the one or more operating parameters of the pressure relief system may be timing of opening of the at least one pressure relief valve, duration of opening of the pressure relief valve, and pressure pulse frequency, which may be useful to control if the pressure relief system includes an active valve. However, the pressure relief system will typically include a passive valve (e.g., a blowoff valve) configured to open when the input pressure exceeds its cracking pressure. Moreover, the effective cracking pressure may be modulated by adjusting (positively or negatively) the pressure of gas or vacuum applied to either side of the blowoff valve. The one or more operating parameters of the vacuum system may be vacuum pulse frequency, vacuum pulse duration, and vacuum pulse amplitude. The delivery devices will also generally include a gas propellant system and a constant positive pressure mechanism having one or more operating parameters capable of being controlled by a user. For example, operating parameters of the gas propellant system may include gas pulse frequency, gas pulse duration, and gas pulse amplitude. An exemplary operating parameter of the constant positive pressure mechanism may be positive pressure amplitude.

Other systems or features, such as a gas propellant system and/or a constant positive pressure mechanism may be included in the devices and have one or more operating parameters, wherein the device interface is configured to receive input from a user that defines the one or more operating parameters. The one or more operating parameters of the gas propellant system may be gas pulse frequency, gas pulse duration, and gas pulse amplitude. An operating parameter of the constant positive pressure mechanism may be positive pressure amplitude.

The operating parameters input by the user can be used to generate a variety of pulses having a pulse pattern (that include, e.g., gas pulses and vacuum pulses, that may be collectively referred to as sub-pulses) capable of being tailored to various tissues. In some variations, the pulse pattern includes one or more gas pulses and one or more vacuum pulses. For example, the pulse pattern may consist of a single gas pulse and multiple vacuum pulses or a single vacuum pulse and multiple gas pulses. The amplitude and/or duration of any of these pulses and sub-pulses may also be manipulated by the user.

The delivery devices may comprise a delivery conduit having a proximal end and a distal end. The delivery conduit may be configured to be removably attached to, and extend from, the distal end of the handpiece. The delivery conduit may be provided as a needle, a cannula, or a catheter.

Any suitable molecule may be introduced into the delivery device by loading a removably attachable molecule holder into any suitable portion of the device, where the holder comprises a plurality of molecules. For example, the molecule holder may be loaded into the hub or connector of the delivery conduit (e.g., the needle hub), or attached to the proximal end of the delivery conduit hub or connector. The molecules may be biologically active molecules comprising, but not limited to, a deoxyribonucleic acid (DNA), a ribonucleic acid (RNA), a carbohydrate, a protein, a synthetic polymeric construct, a recombinant nucleic acid, a physiological marker probe, a drug, a dendrimer, a vaccine, or combinations and mixtures thereof. In one variation, the molecule alone is delivered by the device (i.e., no particles are used as a carrier for the molecule). In another variation, the molecule is adhered, coupled, or linked to a particle carrier that is delivered by the device. For example, the molecule may be coated onto the particle. In further variations, the molecule comprises a diagnostic marker, e.g., a dye.

Methods for the controlled delivery of molecules are also described herein. Some of the methods include the steps of selecting one or more operating parameters of a plurality of device systems of a delivery device via a user interface of the device to generate a pulse pattern, loading particles into the device, positioning the device or a portion thereof adjacent to or into a target tissue; flowing a pressurized gas through an acceleration lumen of the device; and controllably delivering the molecules into the target tissue according to the selected operating parameters. An exemplary device may include a handpiece having a body, the body comprising a proximal end, a distal end, and an acceleration lumen therebetween in fluid communication with the pressurized gas source; a device interface configured to receive input from a user, where the input defines one or more operating parameters of the plurality of device systems; and a control module linked to the device interface, and configured to execute the one or more operating parameters of the systems according to the user input. As previously stated, the operating parameters input by the user can be used to generate a variety of pulses having a pulse pattern (that include, e.g., gas pulses and vacuum pulses, that may be collectively referred to as sub-pulses) capable of being tailored to various tissues. In some variations, the pulse pattern includes one or more gas pulses and one or more vacuum pulses. For example, the pulse pattern may consist of a single gas pulse and multiple vacuum pulses or a single vacuum pulse and multiple gas pulses. The amplitude and/or duration of any of these pulses and sub-pulses may also be manipulated by the user.

Kits for delivering molecules into tissue comprising the delivery devices, and one or more molecule holders are also described herein. Commercially available needles and/or needle adapters for connecting the needles to the handpiece of the device may also be included in the kits.

The delivery devices, kits, and methods of delivering molecules, including biologically active molecules, to a target site with the devices find use in a variety of different applications where it may be desirable to introduce a molecule to a target site. Any suitable type of surface or material that can be made accessible to the delivery device may be targeted using the devices, methods, and kits. The target site can be a delicate tissue that is susceptible to damage during particle bombardment at high pressure. Mammalian tissue is an example of a target site that can be used in variations.

The delivery device, kits, and methods of delivering molecules to a target site under low pressure can be applied to a variety of targets including, but not limited to a cell, cell cultures, tissues, organs, animals, animal embryos, bacteria, fungi, algae, cell nuclei and organelles such as chloroplasts and mitochondria. Target tissues of interest include the skin, retina, brain, liver, pancreas, spleen, heart, bladder, kidney, and muscle, for example. Other target tissues may include plants, plant cells, seedlings, cultured plant cells, leaves, epidermal tissues, apical meristems, and floral tissues.

The provided delivery devices, kits, and methods may be configured to facilitate the delivery of any suitable molecule, polymer, material, or active agent to a target site. In certain variations, the devices may find use in the delivery of labeling dyes to a target tissue. In other variations, the devices may find use in the delivery of drugs to a target tissue. General applications of the delivery devices and methods of delivering a molecule to a target site include gene therapy. Gene therapy aims to introduce specific genes into a host to replace defective ones (replacement therapy) or to suppress expression of certain undesirable genes (anti sense therapy). Other potential applications of the delivery devices include the research of gene regulation and promoter analysis, in vivo cellular labeling and imaging, and cellular physiology. The delivery devices, kits, and methods can also be used to further understanding of vaccinations, cancer, infectious disease, and wound healing; to generate immune responses in animals; to assay gene expression and regulation both in vivo and in vitro; and for diagnostic purposes.

BRIEF DESCRIPTION OF THE DRAWINGS

FIGS. 12A-12D depict cross-sectional and partial cross-sectional views of exemplary needle adapter configurations.

DETAILED DESCRIPTION

The delivery devices described here are generally used to deliver biologically active molecules (BAM) to biological tissues in vivo, ex vivo, and in vitro. As previously stated, the devices may are similar to traditional particle bombardment (aka gene guns) devices in that a BAM payload may be complexed onto the surface of gold or tungsten micro/nanoparticles and subsequently propelled at high velocity into a target tissue via a pressurized gas source. It is understood that in some instances the molecules can be delivered without a carrier particle (i.e., the BAM may be "naked" and not complexed to or otherwise associated with a particle). However, unlike these known particle bombardment devices, the devices described herein incorporate multiple systems that may enable direct BAM injection to a target tissue via a needle, catheter, or cannula with minimal or no tissue damage. The integration of operating parameters of the systems, e.g., by a control module, enable the user to control BAM delivery performance, which can be tailored to the wide variety of potential target tissues throughout the body (e.g. muscle, connective tissue, skin, nervous tissue, etc.). It is this controlled and tailored delivery of molecules that may be particularly useful.

I. Delivery Devices

The controlled and tailored delivery of molecules, including biologically active molecules, and molecules associated with particles, from the devices described here may be effected by altering or adjusting various operating parameters of the systems generally included in the devices, e.g., a gas propellant system, a vacuum system, a pressure relief system, and/or constant positive pressure system (or mechanism), and as further described below. The operating parameters may include pulse frequencies, pulse amplitudes, pulse durations, positive pressure amplitudes, etc. Other features beneficial for particle deployment, such as illumination components or positioning components, may also be included in the delivery devices.

The delivery devices for delivering molecules may include a source of pressurized gas for acceleration of a molecule; a handpiece having a body, the body comprising a proximal end, a distal end, and an acceleration lumen therebetween in fluid communication with the pressurized gas source; a device interface configured to receive input from a user, where the input defines one or more operating parameters of a plurality of device systems; and a control module linked to the device interface, and configured to execute the one or more operating parameters of the systems according to the user input to generate a pulse pattern. The source of pressurized gas may include any suitable gas, e.g., nitrogen, argon, xenon, carbon, dioxide, air, helium, or mixtures thereof. The body may be elongate or have any suitable configuration that allows the user to comfortably and stably hold the handpiece.

Figure 3:
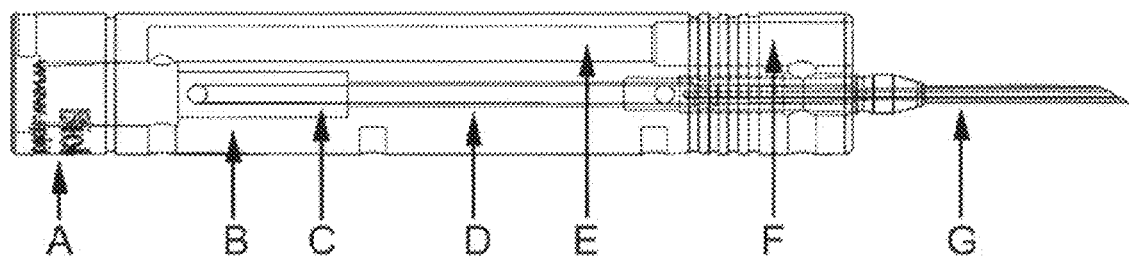
FIG. 3 depicts a cross-sectional view of the handpiece in FIG. 1.

The handpiece of the delivery device generally serves multiple purposes: 1) it provides a mounting location to attach the needle, 2) it provides a mounting location for the particle holder, 3) it provides a mounting location for the illumination source (LED, laser) if included, 4) it conveys the pressurized gas and vacuum from the flexible tubing (from the control module) to the needle/particle holder, 5) it contains a pressure relief valve(s), 6) it conveys low pressure constant gas to the needle tip/tissue interface, and 7) it provides the user with an ergonomic handle to comfortably position the delivery conduit, (e.g. needle), either freehanded or stereotaxically, to the desired target site. The delivery handpiece may be fabricated from any suitable metal (e.g., aluminum, stainless steel, titanium) or any suitable polymer (e.g., ABS, acetal, nylon). The handpiece may also be sized and shaped so that it is sufficiently light in weight to hold in the hand comfortably for extended periods of time or to be securely mounted to a stereotaxic micromanipulator via mounting holes. At its distal end, the handpiece may include appropriate airtight fillings (e.g. Luer lock) to securely mount the needle/particle holder. The handpiece may further allow for attachment of the flexible pressurized gas and vacuum tubing via a freely rotating quick release mechanism to the proximal end. Internally, the handpiece may contain separate chambers for the pressurized gas and vacuum circuits, as well as one or more pressure relief valve(s). For example, and as shown in FIG. 3, a handpiece may include a quick release coupling (A), a LED/laser illumination source (B), an optical fiber (C), a gas pulse port (D), a vacuum scavenging port (E), a pressure relief valve (F), and a needle (G).

The delivery conduit of the delivery devices described here may be provided as a needle, a cannula, or a catheter. In one variation, the delivery conduit is a needle. The delivery conduit is generally attached to the handpiece distal end using a coupling such as a Luer lock (or similar) fitting. The delivery conduit enables the user to deliver the BAM coated micro/nano-particles into the body (e.g., subdermal, intraocular, intracranial, intrathecal, intrathoracic, intra-abdominal, etc.) to a target tissue.

Figure 4:
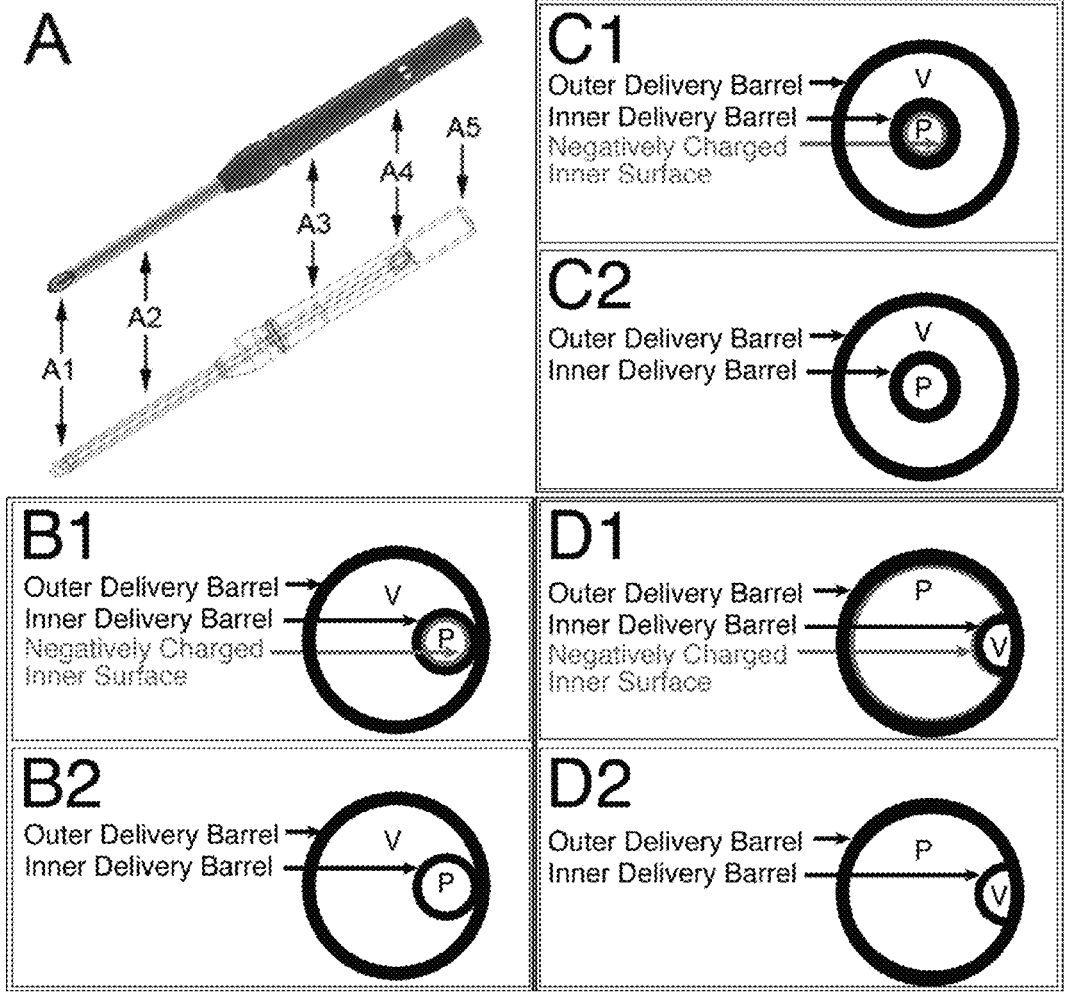
FIG. 4 shows various views of delivery conduit.

The delivery conduit (needle, catheter, or cannula) may be composed of any suitable metal (e.g., aluminum, stainless steel, titanium, or alloy thereof) or polymer (e.g., ABS, acetal, nylon), or a combination thereof. Typically, the needle shaft is composed of metal, while the hub is composed of a polymer, but variations may include all metal or all polymer-based needles. The needle shaft tip may be either blunt or sharp, with a variety of point styles and gauges. Internally, the needle may contain multiple isolated channels or lumens to separate the pressurized gas pulse from the vacuum scavenging pulse. The pressurized gas and vacuum scavenging channels or lumens may combine at the distal end of the needle, adjacent to the target tissue. These isolated channels or lumens may be composed of either rigid or flexible metal or plastic tubing, or may be manufactured (e.g. molded or machined) directly into the needle body. The proximal end of the needle includes an attachment point to mount the micro/nano-particle holder. Internally, the needle may include a negatively (or positively) charged surface coating to facilitate the free flow of micro/nano-particles, molecules, including biologically active molecules, and combinations thereof, through the needle. As shown in FIG. 4, exemplary delivery conduit configurations include an inner particle barrel (lumen) with a wall having a charged (B1, C1, D1)) and uncharged (B2, C2, D2)) inner surface. In B1 and B2, the inner particle lumen is eccentrically disposed within the vacuum lumen. In C1 and C2, the inner particle lumen is concentrically disposed within the vacuum lumen. In D1 and D2, the vacuum lumen is within the wall of the particle lumen (barrel). Although smaller barrels within a larger outer barrel are depicted in FIG. 4, it is understood that alternative configurations can be employed. For example, a smaller barrel could be attached to the outside surface of a larger barrel.

Figure 12B:
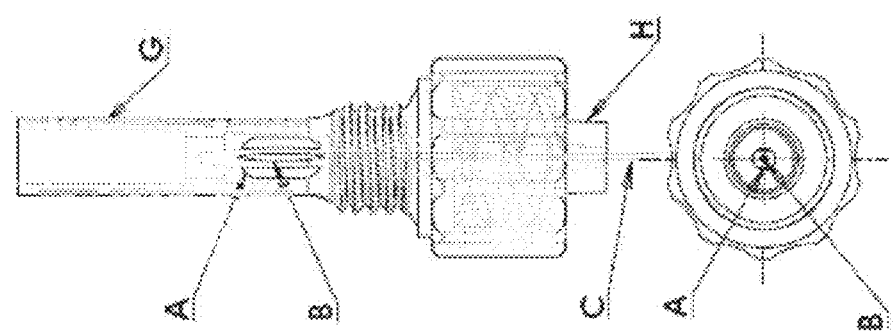
Figure 12A:
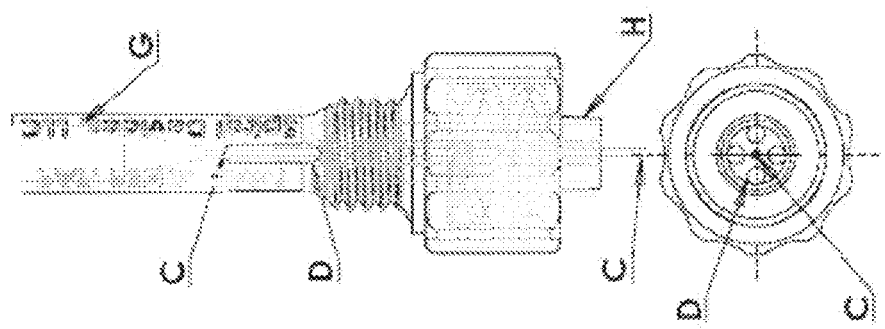

In some variations, commercially available needles are used as the delivery conduit. Here an adapter may be employed to releasably secure the needle to the handpiece. The adapters may be an integrated component of the handpiece or provided as a separate component that can be attached to the handpiece. Generally, a male luer fitting is provided on the adapter, and a female luer is provided on the needle. The adapters may include an inner barrel that is in fluid communication with an inner lumen of the device, and may connect the inner barrel of the adapter, which extends past the distal end of the adapter, to the needle lumen. This inner barrel may be made as part of the adapter or added on after adapter fabrication. In one variation, the inner barrel of the adapter conveys vacuum to the needle tip when a needle is connected. In another variation, the inner barrel of the adapter delivers pressurized gas and particles to the needle tip when a needle is attached. For example, as shown in the adapter of FIG. 12A, particles may be propelled through an outer lumen (A), while vacuum is applied to an inner lumen (B). Inner lumen (B) is in fluid communication with inner barrel (C) that extends inside the shaft of a standard luer lock needle (not shown) attached to the male luer (H) at the distal end of the adapter. Here particles are loaded into the proximal end (G) of the adapter. Alternatively, as shown in the adapter variation of FIG. 12B, particles may be propelled through an inner barrel (C), while vacuum is applied to the outer four lumens (D). The inner barrel (C) extends inside the shaft of a standard luer lock needle (not shown) attached to the male luer (H) at the distal end of the adapter. Particles in FIG. 12B are loaded into the proximal end (G) of the adapter.

Some variations of the adapter may include a single central lumen for the delivery of particles and gas, and a relief port for the application of vacuum. In these variations, the single central lumen may have a constant diameter or a diameter that decreases distally to form a tapered lumen. For example, as shown in FIG. 12C, particles may be propelled through a single central lumen (I) having a constant inner diameter lumen while vacuum is applied to a relief port(s) (E). A standard luer lock needle (not shown) is attached to the male luer (H) at the distal end of the adapter. Particles are loaded into the proximal end (G) of the adapter. Another exemplary needle adapter is shown in FIG. 12D, where particles may be propelled through a single central tapered lumen (J) while vacuum is applied to a relief port(s) (F). A standard luer lock needle (not shown) is attached to the male luer (H) at the adapter distal end. Particles are loaded into the proximal end (G) of the adapter.

Figure 1:
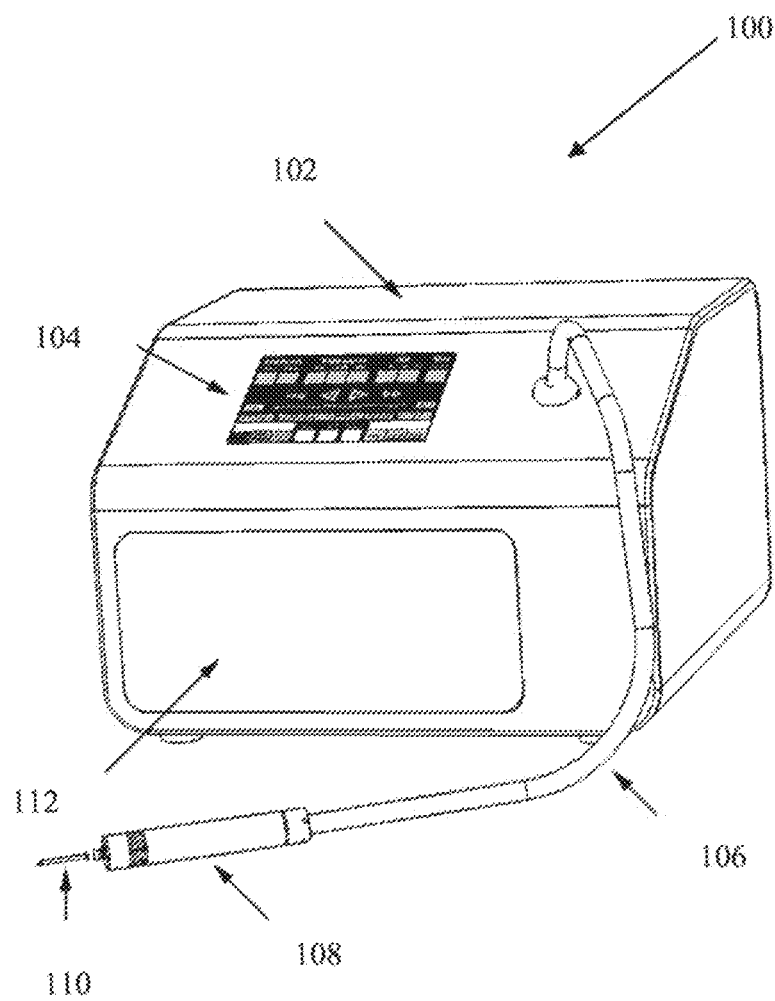
FIG. 1 depicts a perspective view of an exemplary molecule delivery device.
Figure 2:
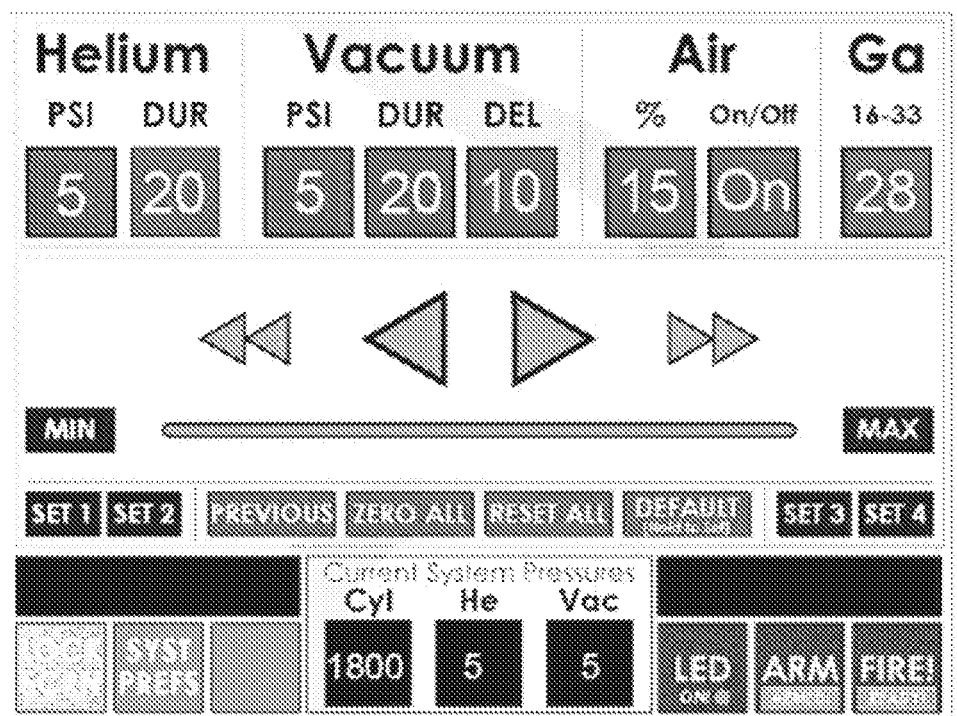
FIG. 2 is an expanded view of the user interface shown in FIG. 1.

Referring to FIG. 1, an exemplary delivery device (100) includes a control module (102) and a user interface (104) on the control module. Here the user interface (shown in greater detail in FIG. 2) is a touch screen LCD, but any suitable user interface may be employed. The various systems of the delivery devices may be controlled via the user interface (104) by a user or operator inputting or selecting various operating parameters of the systems. Flexible tubing with multiple lumens (106) connects a source of pressurized gas (not shown) housed within the control module (102) to a handpiece (108). The pressurized gas is used to accelerate particles through at least a portion of the handpiece (108) and a delivery conduit (110) to a target site in tissue (not shown). A drawer (112) for storing device components may be provided with the device if desired.

The particles (i.e., carrier particles) delivered by the devices described herein include, but are not limited to, elemental particles of a heavy metal such as gold, silver, or tungsten, as well as non-metallic polymers. The size of the particles may vary, and are in some instances on the micrometer or nanometer scale, e.g., ranging from 10 nm to 10 µm. The particles can be coated with a biologically active molecule or material before they are delivered to the target site. Exemplary biologically active molecules include but are not limited to, deoxyribonucleic acid (DNA), ribonucleic acid (RNA), a carbohydrate, a protein, a synthetic polymeric construct, a recombinant nucleic acid, or mixtures and combinations thereof. Other materials that can be delivered via the particles include, but are not limited to, marker dyes, drugs, and complex macromolecules, e.g., dendrimers and vaccines. As previously stated, in some variations no carrier particle is employed, and a naked molecule is delivered by the devices. Here the molecules may be compacted (e.g., compacted nucleic acids, carbohydrates, proteins, etc.).

In some variations, the biologically active molecules may be provided on a removably attachable molecule holder, which can be loaded into the needle hub near its proximal end, and then subsequently loaded into the handpiece distal end as an assembly. Any suitable molecule holder may be employed, so long as it is capable of immobilizing the molecules/particles comprising a BAM onto a surface and releasing those molecules/particles with only the application of a pressurized gas pulse or by altering the charge of the holder substrate.

Figure 5:
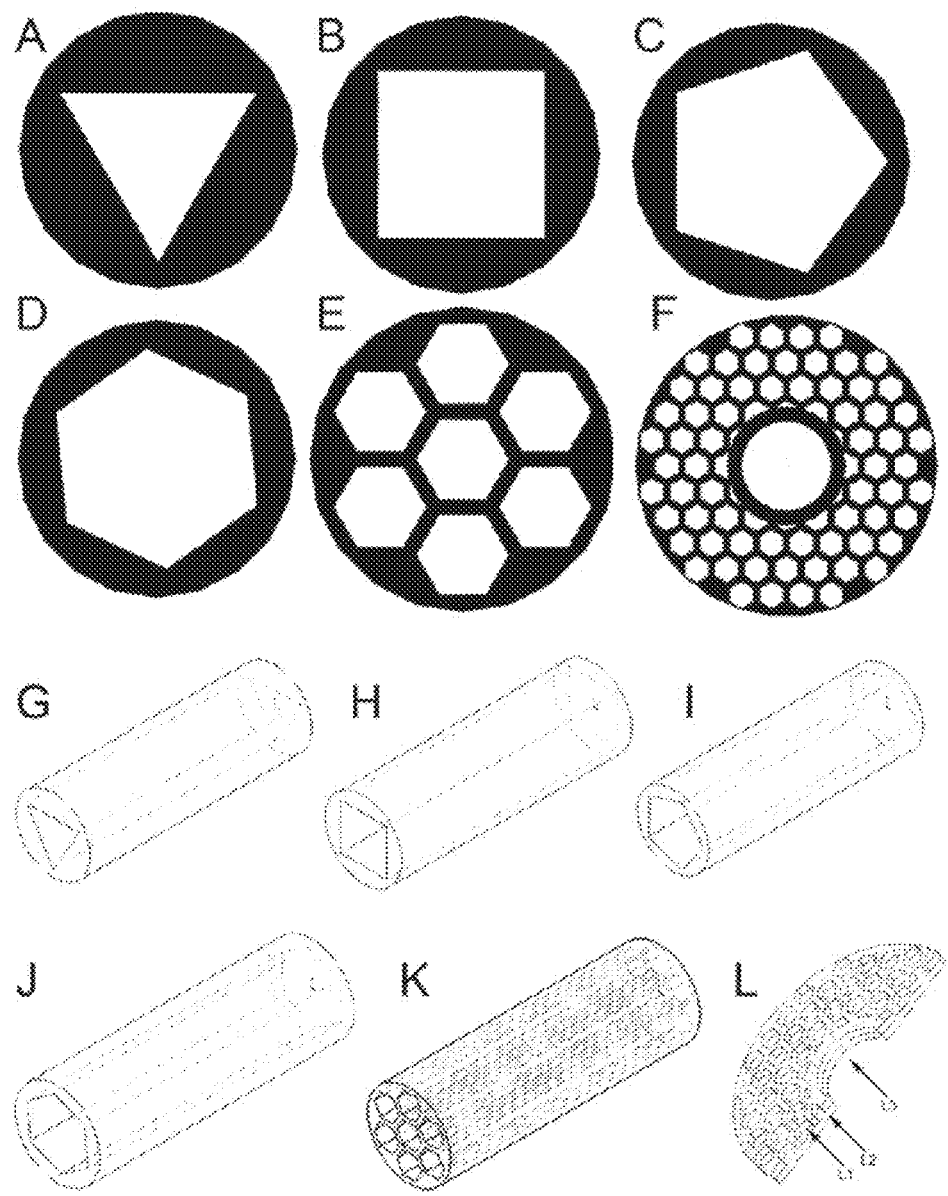
FIG. 5 depicts various views of exemplary molecule holders.
Figure 6:
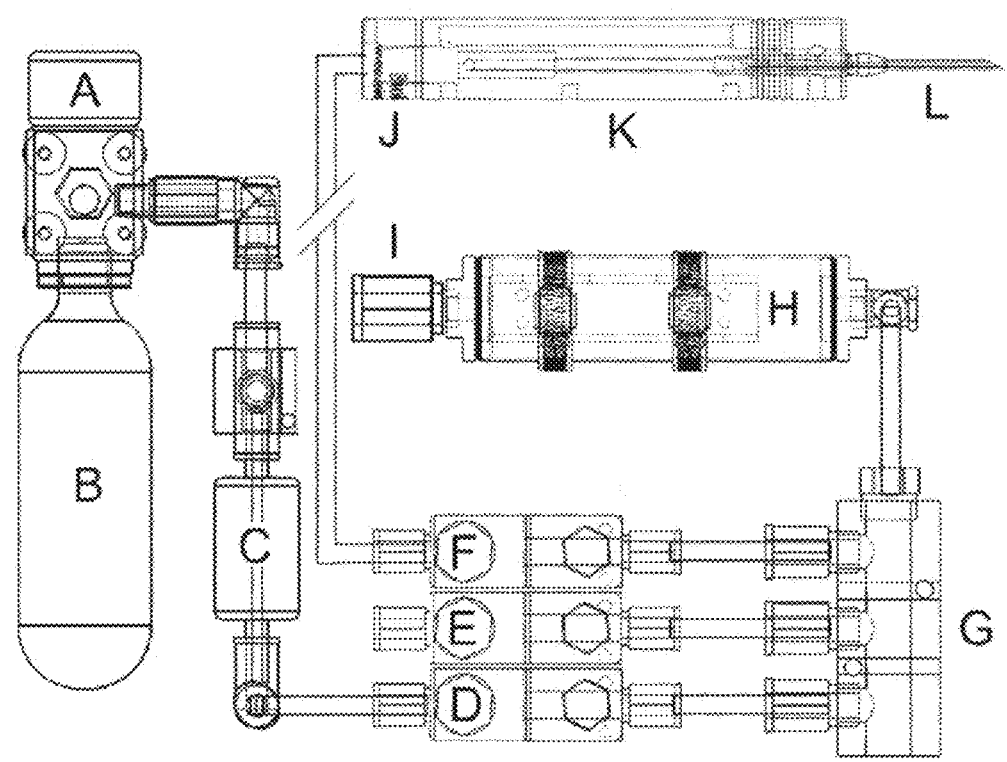
FIG. 6 depicts a schematic view of an exemplary gas propellant system.
Figure 7:
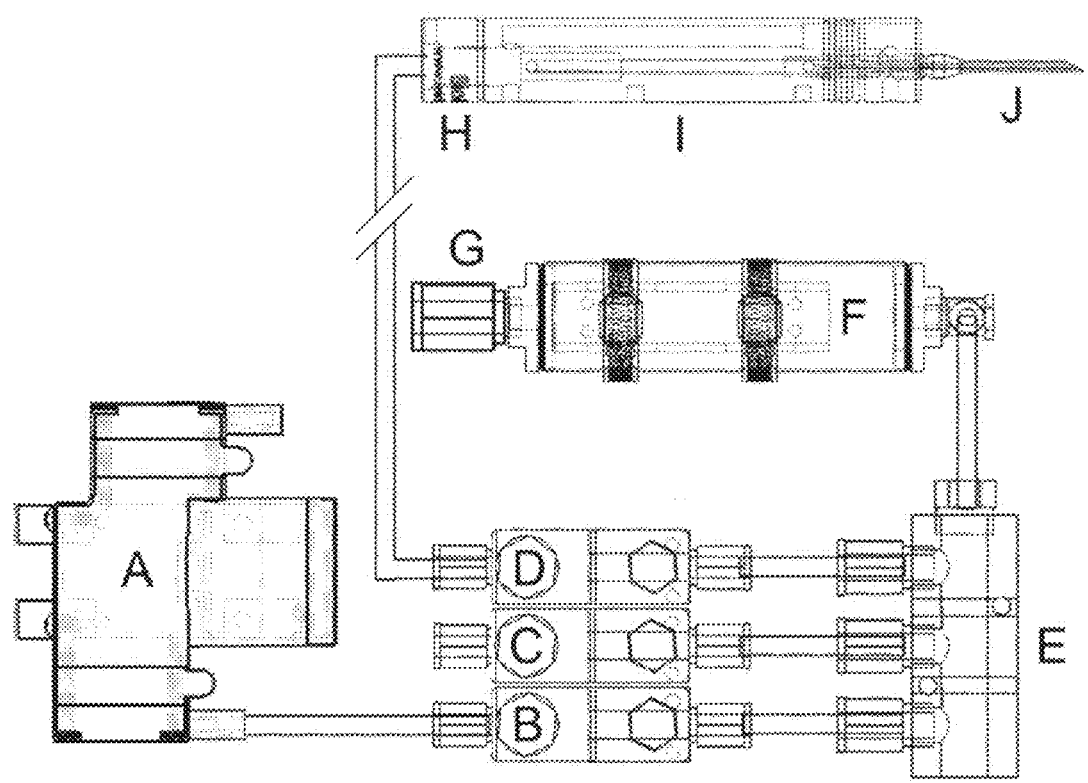
FIG. 7 shows a schematic view of an exemplary vacuum system.
Figure 8:
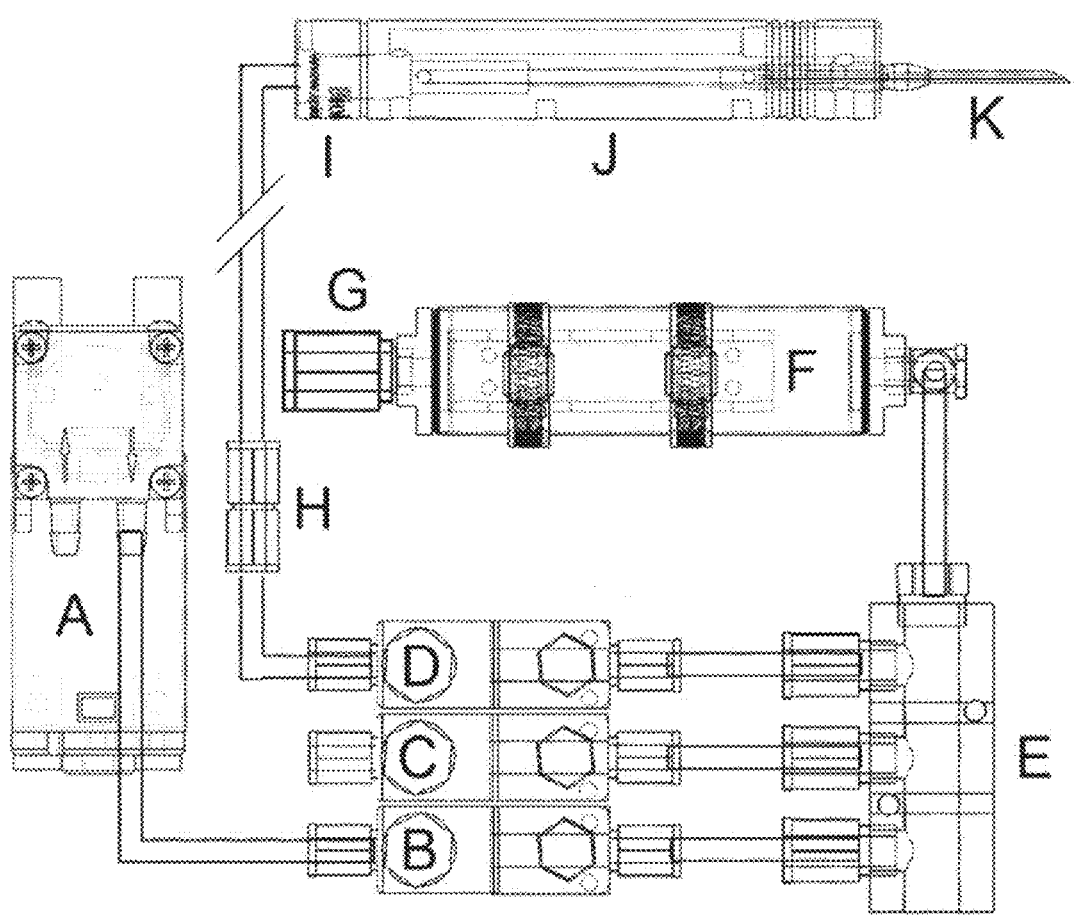
FIG. 8 depicts a schematic view of an exemplary constant positive pressure mechanism.

The holder may be composed of a plastic polymer (e.g., PTFE, PEEK, FEP, Nylon, Teflon) or a suitable metal (e.g., copper, nickel, tungsten, titanium, gold). The holder exterior is typically cylindrical, however other shapes and geometries may be used. The holder interior may have a single lumen or a plurality of lumens with a variety of cross sectional profiles as shown in FIG. 5, including triangular (A), square (B), pentagonal (C), and hexagonal (D), or multi-lumen hexagonal (E, F). The holders will usually have a central open region that allows the free passage of gas, vacuum, and/or illumination, as shown in FIG. 4 (G-K). The 3D length of the holder may be one or more centimeters long in some cases, or significantly shorter in length such that it resembles a 2D disc (L) similar to those used for electron microscopy (e.g., EM grids). The molecule/particle binding surface may be positively or negatively charged in order to facilitate the binding and/or selective release of the molecules/particles at the appropriate time. The molecules/particles themselves may be adhered to the holder via the use of a polymer such as polyvinylpyrrolidone (PVP).

The delivery devices described herein typically include a user interface. The user interface, including the variation shown in FIGS. 1 and 2, generally enables the user to control and monitor all aspects of the device. The user interface may be incorporated into the control module and may seamlessly integrate user inputs, control and coordinate system functions and activity, and resultant output (micro/nano-particle delivery). The structure of the user interface may comprise a touch screen LCD display with graphics, integrated microcontroller, and custom software code. In use, the interface generally enables control and observation of the following operating parameters:

A. Gas propellant system
 1. Gas pulse arming and triggering (also triggerable via a foot pedal)
  2. Gas pulse duration(s) (onset and offset)
  3. Gas pressure amplitude(s)
  4. Gas pulse frequency, pulse duration, and pulse amplitude can be independently manipulated to alter the overall shape of the gas pulse waveform.
- B. Vacuum system
  1. Vacuum pulse trigger and timing relative to gas pulse
  2. Vacuum amplitude(s) regulation
  3. Vacuum duration (s) (onset and offset)
  4. Vacuum pulse frequency, pulse duration, and pulse amplitude can be independently manipulated to alter the shape of the vacuum pulse waveform.
- C. Constant positive pressure system/mechanism
  1. Positive pressure trigger (typically constant)
  2. Positive pressure amplitude
- D. Pressure relief system
  1. Timing of opening of one or more pressure relief valves (that operate in a passive or active mode)
  2. Duration of opening of one or more pressure relief valves
- E. Data storage and retrieval
  1. Data logger for all device set-point and monitor parameters
  2. Data download/upload via USB/WiFi
  3. "Wizard" to guide in optimal device parameters for various experimental conditions
  4. Standard presets for common experimental conditions
  5. Custom protocol save and recall
- F. System monitors
  1. Current supply gas cylinder pressure monitor
  2. Current gas system pressure monitor
  3. Current vacuum system pressure monitor
- G. Illumination
  1. Field illumination intensity
  2. Aiming illumination ON/OFF
- H. Ultrasound positioning
  1. Display of ultrasound image
  2. Selection and magnification of regions of interest
- I. Maintenance
  1. Control of access drawer for maintenance of gas cylinder(s) and filters
  2. Automated device maintenance/sterilization cycle (gas/chemical/heat)
  3. Auto-calibration mode via an externally accessible pressure sensor
  4. Consumable re-ordering
  5. Online support The above-described user control and monitoring aspects may be accomplished through the use of a central Electronic Control System (ECS) "brain" in the device. The ECS generally receives and integrates inputs from the user via the user interface as well as multiple system monitoring sensors (e.g. pressure, temperature, valve state) and outputs both digital and analog commands to multiple peripheral components to achieve a desired firing profile. All electronics in the system are powered via either standard wall outlet power (e.g. 110-220 V) or re-chargeable battery pack (e.g. 5-12 V), integrated or offered as an accessory, enabling the device to be completely portable.

The ECS may consist of both hardware and software. The ECS hardware may include a programmable microcontroller that is coupled to ancillary electronic circuit boards, a touch screen LCD, and peripheral electronic components (e.g. actuators, sensors, etc.). All communication (inputs and outputs) between these various components may occur through the programmable microcontroller. The ECS may also include proprietary software code that allows dynamic real time control and communication between all subsystems and monitoring aspects of the system. The language environment may be a standard variety (e.g. C++, Python, Matlab, etc.) commonly used in modern computing that is capable of being shared by all device components.

Gas Propellant System

The delivery devices described herein typically include a gas propellant system. The gas propellant system (GPS) generally enables gas pressure regulation and pulse delivery. A pressurized gas source (e.g. helium, nitrogen, compressed air, etc.) is used to propel molecules, including BAMs, and BAM coated micro/nano-particles at high velocity into a target cell/tissue. The triggering of the gas pulse(s) as well as the pulse duration, frequency, and amplitude can be manipulated via the touch screen user interface. These user commands are output via the programmable microcontroller to a series of solenoid valves, a reservoir, and sensors, to trigger and control the amplitude and timing of the gas pulse (see, e.g., FIG. 6). The desired gas pressure set point may be achieved through precise balance between two solenoid valves consisting of a high-pressure gas inlet (direct from the pressurized cylinder) and an exhaust to atmosphere. One or more holding reservoirs in fluid communication with a gas pressure sensor(s) is used to store an appropriate quantity(ies) of pressurized gas sufficient to propel (according to the user chosen profile) the molecules/BAMs/BAM coated micro/nano-particles into a target tissue. Triggering of the pressurized gas pulse may be achieved through actuation of yet another solenoid valve. Actuation (and precise timing thereof) of all solenoid valves may be ultimately controlled via the programmable microcontroller that receives inputs from the user defined set points and pressure sensor. The gas pulse is transmitted via flexible tubing to a handpiece containing a molecule holder. The pulse propels molecules/BAMs/BAM coated micro/nano-particles at high velocity through a delivery conduit, e.g., a needle, to the target site. In total, the hardware components of the GPS include: solenoid valves, pressure sensor, pressurized gas cylinder, reservoir chamber, solenoid driver circuitry, touch screen LCD, and programmable microcontroller. In some variations, and as shown in FIG. 6, the GPS system may include a fixed pressurized gas regulator (A), a pressurized gas cylinder (B), a filter (C), a gas inlet solenoid valve (D), a gas outlet solenoid valve (E), a gas pulse solenoid valve (F), a manifold (G), a reservoir chamber (H), a pressure sensor (I), a quick release coupling (J), a delivery handpiece (K), and a needle (L). In other variations, an electronic pressure controller (EPC) or electronic pressure regulator (EPR) type system may be employed to modulate the desired pulse pressure and timing. One or more gas propellant systems may be utilized in the device to enable the delivery of multiple discrete propellant pulses (e.g., of unique timing and/or amplitude) in either series or parallel.

Vacuum System

The delivery systems described herein typically also include a vacuum system. The vacuum system (VS) may be provided to counter-balance and scavenge the potentially destructive shock wave resulting from the pressurized gas pulse. Vacuum is introduced at appropriate timing, duration, and amplitude to best counter the pressurized gas pulse. More specifically, vacuum may be provided via a compact vacuum pump that is integrated into the device control module. Alternatively, vacuum can be provided via a "house" vacuum line.

The VS may be structured similarly to the GPS described above. Triggering of the vacuum pulse as well as the pulse duration, frequency, and amplitude are generally all manipulated via the touch screen user interface. These user commands may be output via the programmable microcontroller to a series of solenoid valves (or electronic pressure controllers/regulators), vacuum pump, reservoir, and sensors, to trigger and control the amplitude and timing of the vacuum pulse. In one variation, as shown in FIG. 7, the user commands are output via the programmable microcontroller to a VS comprising a vacuum pump (A), a vacuum inlet solenoid valve (B), a vacuum outlet solenoid valve (C), a vacuum pulse solenoid valve (D), a manifold (E), a reservoir chamber (F), a pressure sensor (G), a quick release coupling (H), a delivery handpiece (I), and a needle (J), to trigger and control the amplitude and timing of the vacuum pulse. One or more vacuum systems may be utilized in the device to enable the delivery of multiple discreet vacuum pulses (e.g., of unique timing and/or amplitude) in either series or parallel.

The desired vacuum pressure set point may be achieved through precise balance between two solenoid valves consisting of a vacuum inlet (direct from the vacuum pump) and an outlet to atmosphere. A holding reservoir in fluid communication with a vacuum pressure sensor may be used to store an appropriate quantity of regulated vacuum sufficient to scavenge the gas pulse used to propel the BAM coated micro/nano-particles to a target. Triggering of the regulated vacuum pulse may be achieved through actuation of yet another solenoid valve. Actuation of all solenoid valves may be ultimately controlled via the programmable microcontroller that receives inputs from the user defined set points and pressure sensor. The vacuum pulse is conveyed via flexible tubing to the handpiece containing a custom multiple lumen needle that is capable of initially isolating and ultimately combining the vacuum and gas pulses at the appropriate location. In some variations, the hardware components of the VS include: solenoid valves, a pressure sensor, a vacuum pump, a reservoir chamber, solenoid driver circuitry, a touch screen LCD, and a programmable microcontroller.

Constant Positive Pressure System/Mechanism

The delivery devices described herein typically include a constant positive pressure system or mechanism. The constant positive pressure (CPP) system/mechanism is generally employed to prevent aqueous liquids (e.g., blood, lymph, aqueous humor, cerebral spinal fluid, water, saline, etc.) from entering the device delivery conduit, e.g., needle, during the BAM delivery procedure. CPP may be provided via a compact low-pressure source (e.g., air pump, pressurized gas cylinder, etc.). The user (or wizard) defined amplitude of the CPP may be controlled via electronic speed control of the air pump through the use of a pulse width modulated (PWM) output from the programmable microcontroller. In the case of CPP from a pressurized gas cylinder, an electronic regulator system may be used similarly to the solenoid valve based gas pulse and vacuum systems described above. CPP is typically conveyed to the handpiece via flexible tubing and ultimately to the target tissue via the delivery conduit (e.g., needle, cannula, or catheter), as described herein. In some variations, the CPP system is comprised of an air pump (or gas cylinder), one-way valves, driver circuitry, solenoid valves, touch screen LCD, and programmable microcontroller. One exemplary CPP system is shown in FIG. 8. Referring to the figure, the CPP system comprises an air pump (A), an air inlet solenoid valve (B), an air outlet solenoid valve (C), a handpiece outlet solenoid valve (D), a manifold (E), a reservoir chamber (F), a pressure sensor (G), a one-way valve (H), a quick release coupling (I), a delivery handpiece (J), and a needle (K).

Pressure Relief System

The delivery devices described herein typically include a pressure relief system. The pressure relief system (PRS) may serve to mitigate the potentially destructive effects of the pressurized gas pulse. The PRS may act in either a passive or active manner by providing a shunt for excessive pressurized gas to vent to atmosphere, thereby preventing the gas pulse shock-wave from damaging delicate biological tissues.

In some variations, the PRS is comprised of one or more passive pressure relief valves with a pre-set or variable "cracking" pressure. The relief valves may be located in the delivery handpiece, connective tubing, and/or in the control module. A variable relief pressure point may be achieved by application of positive pressure (e.g., gas or air) to the backside (reverse direction) of the relief valve, resulting in a net increase/decrease of relief "cracking" pressure. Active electronically adjustable pressure regulators may also be used with an adjustable pressure relief orifice.

Illumination System/Component

In some variations, the delivery devices include an illumination system or illumination component. The illumination system (IS) may be generally designed to assist in both the visualization of the target site and precise positioning of the delivery handpiece. The illumination system may be a high intensity LED (or laser) integrated directly into the handpiece itself or into a quick release coupling attaching the handpiece to the flexible gas/vacuum tubing. Alternatively, the illumination source can be located in the control module and light transmitted to the handpiece via optical fiber. Illumination may be conveyed to the target site through the inner diameter of the needle to facilitate precise handpiece/delivery conduit (e.g., needle) positioning and BAM delivery. Illumination intensity may be provided via user input to the user interface and a variable intensity LED driver circuitry through the use of a pulse width modulated (PWM) output from the programmable microcontroller. In one variation, the illumination system may be comprised of a high intensity LED (or laser), associated hardware, electronic driver circuitry, touch screen LCD, and programmable microcontroller.

Ultrasound Positioning System/Component

Some variations of the delivery device may include an accessory ultrasound probe to facilitate delivery conduit (e.g., needle) positioning relative to bodily organs during the delivery procedure. Standard or high-resolution medical/veterinary ultrasound is usually suitable for needle positioning. The ultrasound positioning system (UPS) may be either a standalone system or preferably incorporated directly into the particle bombardment control module. An integrated UPS may present the ultrasound image directly to the device touch screen LCD display. Regions (e.g., in vivo tissue targets) of interest may be selected on the user interface by the user for greater magnification and scrutiny. The ultrasound probe may be attached directly to the main control module and may receive all power directly from the module. In other variations, an accessory screen that plugs into the main control module may also be included in order to concurrently visualize the needle tip and readily modify operating parameter settings.

As previously stated, but provided in more detail here, the particles may include, but are not limited to, elemental particles of a heavy metal such as gold, silver, or tungsten. The size of the particles may vary, and are in some instances on the micrometer or nanometer scale, e.g., ranging from 10 nm to 10 μm. The particles can be coated with a material before they are delivered to the target site. In certain variations, the elemental particle can be coated with an active agent. In certain variations, the elemental particle can be coated with a polymer such as deoxyribonucleic acid (DNA), ribonucleic acid (RNA), a carbohydrate, a protein, and other biological materials, or mixtures thereof, including synthetic polymeric constructs, e.g., recombinant nucleic acids, non-naturally occurring proteins, peptide nucleic acids, etc. Other active agents that can be delivered by way of the particle delivery devices include, but are not limited to, marker dyes, drugs, complex macromolecules, e.g., dendrimers, and vaccines.

II. Methods

Figure 9:
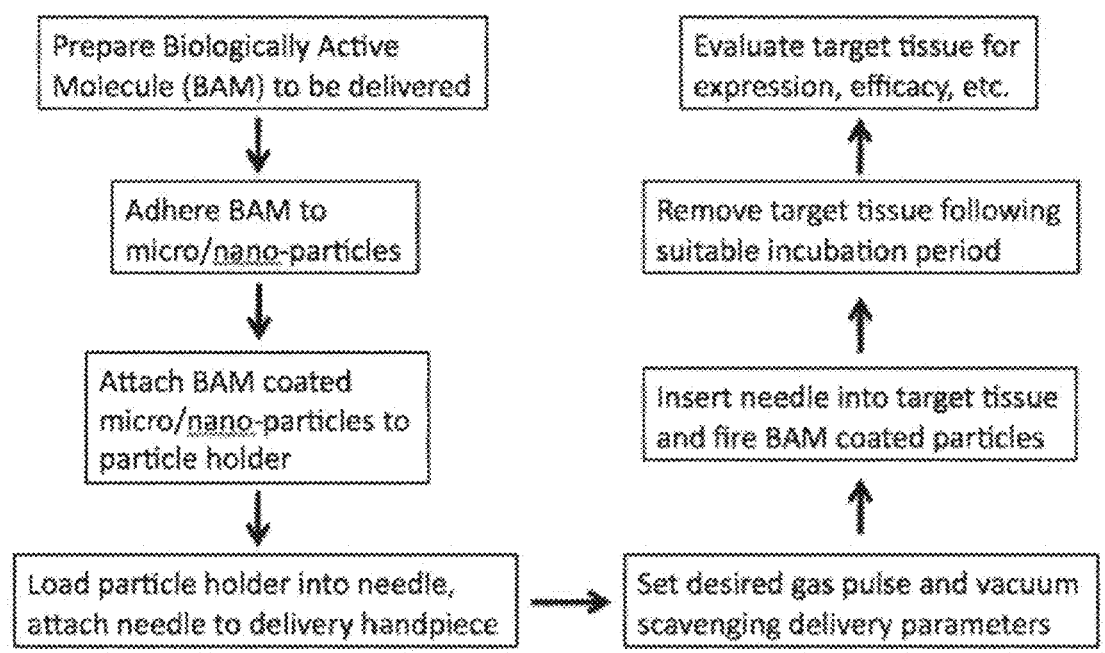
FIG. 9 illustrates the steps included in an exemplary method of controllably delivering particles.

Also provided are methods for the controlled delivery of molecules, including biologically active molecules, and carrier particles associated with (e.g., complexed to, adhered to, coated with, etc.) a molecule, to a target site. In some variations, the method includes the steps of selecting one or more operating parameters of a plurality of device systems of a delivery device via a user interface of the device to generate a pulse pattern, loading a plurality of molecules into the of the device, positioning the device or a portion thereof adjacent to or into a target tissue; flowing a pressurized gas through an acceleration lumen of the device; and controllably delivering the molecules into the target tissue according to the selected operating parameters. An exemplary device may include a handpiece having a body, e.g., an elongate body, the body comprising a proximal end, a distal end, and an acceleration lumen therebetween in fluid communication with the pressurized gas source; a device interface configured to receive input from a user, where the input defines one or more operating parameters of the plurality of device systems; and a control module linked to the device interface, and configured to execute the one or more operating parameters of the systems according to the user input. In other variations, and as illustrated in FIG. 9, the method may include the steps of preparing a biologically active molecule (BAM) to be delivered, adhering the BAM to a particle, attaching the BAM coated particles to a particle holder, loading the particle holder into a delivery device (e.g., into the needle), attaching the needle to a delivery handpiece, selecting gas pulse and vacuum scavenging (vacuum system) parameters, inserting the needle into a target tissue, and triggering an actuator to deliver the BAM coated particles. The methods may further include removing the target tissue following a suitable incubation period and evaluating the tissue for expression, efficacy, etc.

As previously stated, operating parameters of the pressure relief system may be timing of opening of the at least one pressure relief valve, duration of opening of the pressure relief valve, and pressure pulse frequency, which may be useful to control if the pressure relief system includes an active valve. However, the pressure relief system will typically include a passive valve (e.g., a blowoff valve) configured to open when the input pressure exceeds its cracking pressure. Moreover, the effective cracking pressure may be modulated by adjusting (positively or negatively) the pressure of gas or vacuum applied to either side of the blowoff valve. The one or more operating parameters of the vacuum system may be vacuum pulse frequency, vacuum pulse duration, and vacuum pulse amplitude. The delivery devices will also generally include a gas propellant system and a constant positive pressure mechanism having one or more operating parameters capable of being controlled by a user. For example, operating parameters of the gas propellant system may include gas pulse frequency, gas pulse duration, and gas pulse amplitude. An exemplary operating parameter of the constant positive pressure mechanism may be positive pressure amplitude.

Figure 10:
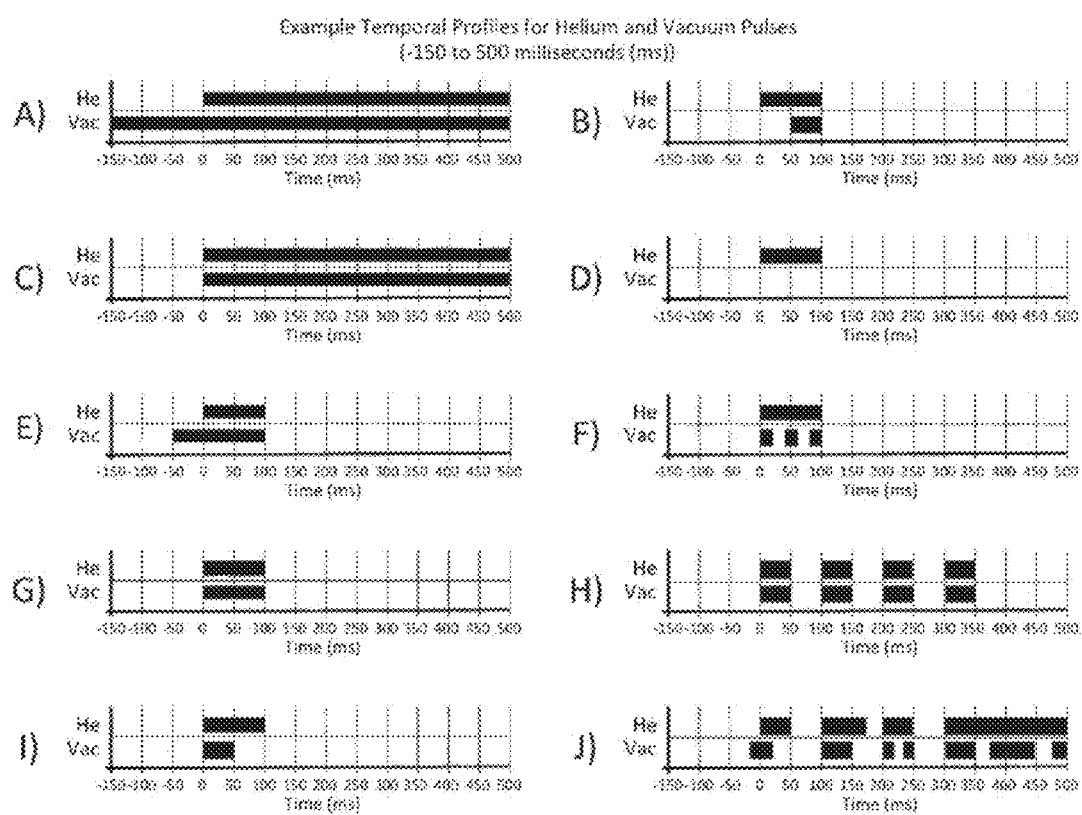
FIG. 10 shows exemplary gas and vacuum pulse patterns.
Figure 11:
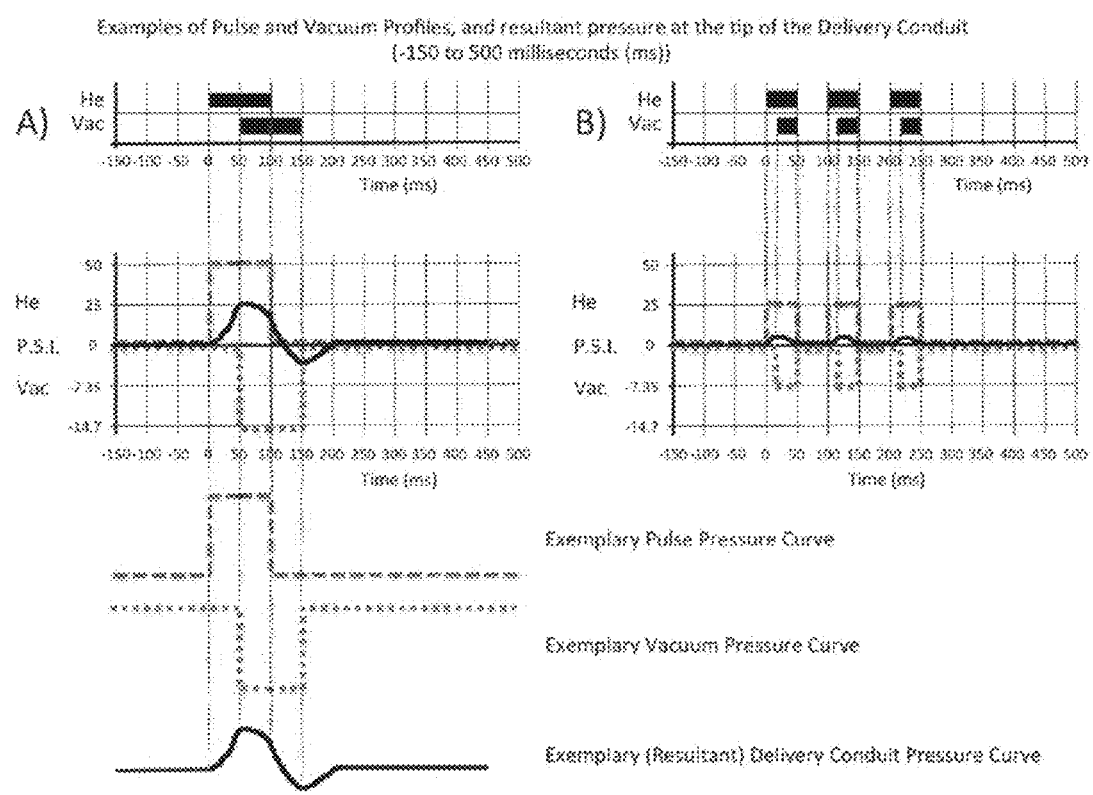
FIG. 11 shows exemplary pulse patterns and their resultant pressure at the tip of a delivery conduit.

The operating parameters input by the user can be used to generate a variety of pulses having a pulse pattern (that include, e.g., gas pulses and vacuum pulses, that may be collectively referred to as sub-pulses) capable of being tailored to various tissues. In some variations, the pulse pattern includes one or more gas pulses and one or more vacuum pulses. For example, the pulse pattern may consist of a single gas pulse and multiple vacuum pulses or a single vacuum pulse and multiple gas pulses (see. e.g., FIG. 10). The amplitude and/or duration of any of these pulses and sub-pulses may also be manipulated by the user to tailor the resultant pressure at the tip of the delivery conduit to a particular tissue. Exemplary gas pulse pressure curves, vacuum pressure curves, and resultant delivery conduit pressure curves are shown in FIG. 11. The gas used for pulsing may be helium.

In some variations, the duration of the gas pulse ranges from about 50 to about 500 milliseconds. In other variations, the duration of the vacuum scavenging pulse ranges from about 25 to about 650 milliseconds. In yet further variations, the vacuum pulse precedes the gas pulse by about 25 to about 150 milliseconds.

Exemplary delivery parameters for select tissues may be as follows:

Retina
    Gas pulse: 10 psi helium pulse with a duration of 10 milliseconds.
    Vacuum scavenging pulse: 16.3 in Hg with a duration of 15 milliseconds, and delay of −5 milliseconds (vacuum precedes the gas pulse).
    Needle gauge: 22

Brain
    Gas pulse: 15 psi helium pulse with a duration of 20 milliseconds.

Vacuum scavenging pulse: 20.4 in Hg with a duration of 25 milliseconds, and a delay of −5 milliseconds (vacuum precedes gas pulse).

Needle gauge: 28

Muscle

Gas pulse: 20 psi helium pulse with a duration of 20 milliseconds.

Vacuum scavenging pulse: 24.4 in Hg with a duration of 25 milliseconds, and a delay of −5 milliseconds (vacuum precedes the gas pulse.

Needle gauge: 18

Positioning of the device or portion thereof adjacent to a target tissue may include positioning the distal end of the delivery conduit adjacent to an in vitro tissue, e.g., at a distance ranging from about 0.05 mm to about 500 mm, or from about 0.5 mm to about 50 mm. In other variations, the target site can be in vivo tissue. In further variations, a needle in fluid communication with the delivery handpiece may be introduced into mammalian tissue. Suitable depths of tissue penetration of the needle may range from about 1 mm to about 500 mm, from about 5 mm to about 250 mm, or from about 10 mm to about 150 mm. For positioning, where desired the system or component(s) thereof can be stereotactically mounted and micro-manipulated with surgical precision. The delivery devices may be loaded with molecules/particles during any suitable portion of the delivery procedure, e.g., prior to or after positioning of the delivery device.

Based on the operating parameters defined by the user, molecules/particles may be controllably delivered into target tissue by triggering an actuator. The actuator may be a component of the delivery device and may comprise any suitable mechanical component capable of being operably coupled to a pressurized gas source. In some instances, the actuator is an electromechanical device that can be actuated manually by a user. Alternatively, the actuator may be actuated automatically by a computer configured to actuate the delivery device. Once actuated, a pressurized gas source coupler in fluid communication with a pressurized gas source provides a pulse of gas through a molecule holder and into the acceleration lumen of the delivery device. The pressure of the gas stream is used to dislodge the molecules/particles from the holder.

In certain variations, the particle delivery device is configured so that a gas stream entering the handpiece at the proximal end has a positive pressure ranging from about 1 to about 100 psi, from about 2 to 50 psi, from about 10 to about 50 psi, or from about 10 to about 20 psi. Once dislodged from the holder, the molecules/particles generally follow the high velocity stream of gas into the delivery device comprising one or more pressure reducing elements positioned between the proximal and distal ends of the handpiece. In some variations, gas entering the proximal end of the handpiece has a velocity of greater than 200 m/sec, greater than 500 m/sec, or greater than 1000 m/sec. In other variations, the gas/particle stream exiting the distal end particle outlet has a velocity greater than 200 m/sec, greater than 500 m/sec, or greater than 1000 m/sec. As described above, the pressure reducing elements of the pressure reducing system moderate the pressure head created by the gas stream so it is less intense when the gas/particle stream reaches the distal end particle outlet of the delivery device.

III. Kits

Kits for delivering molecules and particles, including biologically active molecules, are also provided. The kits may comprise at least include a delivery device as described above and one or more molecule holders. The holders would include a plurality of molecules or particles coated with, or otherwise comprising, biologically active molecules or materials. In some variations, the kits also include a needle or cannula, and/or a needle adapter, as described above, configured to attach to the distal end of the device handpiece.

In addition to above-mentioned components, the kits may further include instructions for using the components of the kit to practice the methods. The instructions for practicing the methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other variations, the instructions are present as an electronic storage data file present on a suitable computer readable storage medium, e.g. CD-ROM, diskette, etc. In yet other variations, the actual instructions are not present in the kit, but means for obtaining the instructions from a remote source, e.g. via the internet, are provided. An example of this variation is a kit that includes a web address where the instructions can be viewed and/or from which the instructions can be downloaded.

The invention claimed is:

1. A method for controlled delivery of molecules comprising:

selecting one or more operating parameters of a plurality of device systems of a delivery device via a user interface of the device to generate a pulse pattern, the device comprising:

a handpiece having a body, the body comprising a proximal end, a distal end, and an acceleration lumen therebetween in fluid communication with a pressurized gas source;

a device interface configured to receive input from a user, where the input defines one or more operating parameters of the plurality of device systems; and a control module linked to the device interface, and configured to execute the one or more operating parameters of the systems according to the user input;

loading a plurality of molecules into the device;

positioning the device or a portion thereof adjacent to or into a target tissue;

flowing a pressurized gas through the acceleration lumen; and controllably delivering the particles into the target tissue according to the selected operating parameters, wherein the pulse pattern comprises one or more gas pulses and one or more vacuum pulses.

2. The method of claim 1, wherein the pulse pattern comprises a single gas pulse and a plurality of vacuum pulses.

3. The method of claim 1, wherein the pulse pattern comprises a single vacuum pulse and a plurality of gas pulses.

4. The method of claim 1, wherein the gas pulse comprises helium.

5. The method of claim 1, wherein the duration of the gas pulse ranges from about 50 to about 500 milliseconds.

6. The method of claim 1, wherein the duration of the vacuum pulse ranges from about 25 to about 650 milliseconds.

7. The method of claim 1, wherein the vacuum pulse precedes the gas pulse by about 25 to about 150 milliseconds.

8. The method of claim 1, wherein the one or more operating parameters of the vacuum system are vacuum pulse frequency, vacuum pulse duration, and vacuum pulse amplitude.

9. The method of claim 1, wherein the plurality of device systems comprises a gas propellant system having one or more operating parameters.

10. The method of claim 9, wherein the one or more operating parameters of the gas propellant system are gas pulse frequency, gas pulse duration, and gas pulse amplitude.

11. The method of claim 1, wherein the plurality of device systems comprises a constant positive pressure mechanism having an operating parameter.

12. The method of claim 11, wherein the operating parameter is positive pressure amplitude.

13. The method of claim 1, wherein the plurality of molecules comprises a biologically active molecule.

14. The method of claim 13, wherein the biologically active molecule comprises a deoxyribonucleic acid (DNA), a ribonucleic acid (RNA), a carbohydrate, a protein, a synthetic polymeric construct, a recombinant nucleic acid, a physiological reporter probe, a drug, a dendrimer, a vaccine, or combinations and mixtures thereof.

15. The method of claim 1, wherein the plurality of molecules comprises a diagnostic marker.

16. The method of claim 1, wherein the target tissue is muscle, connective tissue, skin, nervous tissue, ocular tissue, or a combination thereof.

17. The method of claim 16, wherein the ocular tissue comprises retinal tissue.

18. The method of claim 16, wherein the nervous tissue comprises brain tissue.

\* \* \* \* \*